United States Patent [19]

Cruickshank et al.

[11] Patent Number: 5,258,507
[45] Date of Patent: Nov. 2, 1993

[54] LABELING REAGENTS USEFUL FOR THE CHEMICAL ATTACHMENT OF NITROPHENYL DERIVATIVE LIGANDS TO DNA PROBES

[75] Inventors: Kenneth A. Cruickshank, Naperville; Douglas J. Taron, Elgin, both of Ill.

[73] Assignee: Amoco Corporation, Chicago, Ill.

[21] Appl. No.: 611,161

[22] Filed: Nov. 8, 1990

[51] Int. Cl.⁵ .............................................. C07H 15/12
[52] U.S. Cl. ................................................... 536/24.3
[58] Field of Search ................................ 536/27; 435/6

[56] References Cited

U.S. PATENT DOCUMENTS

| | | |
|---|---|---|
| 4,626,501 | 12/1986 | Landes . |
| 4,828,979 | 5/1989 | Klevan et al. . |
| 4,833,251 | 5/1989 | Musso et al. . |
| 4,849,336 | 7/1989 | Miyoshi et al. . |
| 4,876,395 | 10/1989 | Kissinger . |
| 4,898,951 | 2/1990 | Symons . |
| 4,948,882 | 8/1990 | Ruth . |

FOREIGN PATENT DOCUMENTS

| | | |
|---|---|---|
| 0251283 | 8/1990 | European Pat. Off. . |
| 8606726 | 11/1986 | World Int. Prop. O. . |

OTHER PUBLICATIONS

Lindeman et al. Chemical Abstracts vol. 84, 1976, No. 84:29008.
Kane et al. Abstract 105,538 (1986) No:113404q.
Gall and Pardue, Proc. Natl. Acad. Sci. USA 64: 600 (1969).
John et al., Nature (London) 223: 582 (1969).
Bauman et al., Exp. Cell Res. 128: 485-490 (1980).
Malcolm et al., Ann. Hum. Genet. 45: 135-141 (1981).
Manuelidis et al., J. Cell Biol. 95: 619-625 (1982).
Landegent et al., Exp. Cell Res. 153: 61-72 (1984).
Landegent et al., Nature (London) 317: 175-177 (1985).
Hopman et al., Histochemistry 85: 1-4 (1986).
Landegent et al., Hum. Genet. 73: 354-357 (1986).
Moyzis et al., Chromosoma (Berlin) 95: 375-386 (1987).
van Dekken and Bauman, Cytogenet. Cell Genet. 48 188-9 (1988).
Emmerich et all, Ex. Cell Res. 181: 126-140 (1989).
Pieters et al., Cytogenet. Cell Genet. 53: 15-19 (1990).
van Dekken et al., Cytometry 11: 153-164 (1990).
Cremer et al., Cytometry 11: 110-118 (1990).
Kievits et al., Cytometry 11: 105-109 (1990).
Dale et al., Biochemistry 14: 2447-2457 (1975).
Langer et al., Proc. Natl. Acad. Sci. USA 78: 6633-6637 (1981).
Renz, EMBO 2: 817-822 (1983).
Tchen et al., Proc. Natl. Acad. Sci. USA 81: 3466-3470 (1984).
Draper, Nucleic Acids Res. 12: 989-1002 (1984).
Forster et al., Nucleic Acid Res. 13: 745-761 (1985).
Vincent et al., Nucleic Acids Res. 10: 6787-6796 (1982).
Shroyer and Nakane, J. Cell Biol. 97: Abstract 377a (1983).
Hopman et al., Nucleic Acids Res. 6471-6488 (1986).
Moriuchi et al., Nucleic Acids Res. Symp. Ser. 19: 77-80 (1988).
Keller et al., Anal. Biochem. 170: 441-450 (1988).
Keller et al., Anal. Biochem. 177: 392-395 (1989).
Singh et al., Nucleic Acids Res. 18: 3339-3345 (1990).
Lichter et al., Science 247: 64-69 (1990).
Manning et al., Chromosoma 53: 107-117 (1975).
Rudkin and Stollar, Nature (London) 265: 472-473 (1977).
Hutchinson et al., J. Cell Biol. 95: 609-618 (1982).
Hopman et al., Histochemistry 84: 169-178 (1986).
Garson et al., Nucleic Acids Res. 15: 4761-4770 (1987).

*Primary Examiner*—John W. Rollins
*Attorney, Agent, or Firm*—Norval B. Galloway; William E. Murray

[57] ABSTRACT

This invention discloses methods and compounds for covalently linking nitro-, dinitro- and trinitrophenyl to DNA and the resulting nitro-, dinitro-, and trinitrophenyl labeled DNA reagents. Reagents for the in situ detection of a chromosome or a region of a chromosome are disclosed. These reagents include a multiplicity of DNA sequences that are complementary to different portions of the chromosome or chromosome region to be detected. Multiple nitro-, dinitro- or trinitrophenyl labels are covalently linked to the DNA sequences by means of an amino acid linking group. These labeled reagents are contacted under hybridizing conditions with the chromosome or chromosome region of interest. Any binding of the reagent with the chromosome or chromosome region of interest may then be detected by immunological techniques.

30 Claims, 2 Drawing Sheets

LABELING REAGENTS USEFUL FOR THE CHEMICAL ATTACHMENT OF NITROPHENYL DERIVATIVE LIGANDS TO DNA PROBES

BACKGROUND OF THE INVENTION

1. Field of the Invention

This invention relates to methods and compounds for labeling DNA. The present invention also relates to the detection and identification of chromosomes or regions of chromosomes by hybridization of a multiplicity of different chromosome-specific probes. In particular, this invention relates to in situ hybridization of these chromosome specific probes to chromosomes from disrupted cells that have been prepared so as to leave the native chromosome structure essentially intact and to preserve the physical relationships between different chromosomes, different portions of the same chromosome or between chromosomes and other cellular structures.

2. Summary of the Related Art

In situ hybridization techniques are well known in the art, and have a variety of applications for the detection of chromosomes or regions of chromosomes. These applications include but are not limited to prenatal diagnosis, genetic mapping, somatic cell hybridization and the detection of specific chromosomal genetic markers of malignant and other diseases. Hybridization is performed in situ between chromosomal target DNA sequences and probe sequences that have been modified so as to be detectable by a variety of physical or chemical means after hybridization. Preparation of target chromosomal DNA is performed so as to result in the minimum amount of disruption of chromosomal and cellular structures and to permit hybridization with the probe. Methods for preparation of chromosomal target DNA are well known in the art. (See for example Gall and Pardue, Proc. Natl. Acad. Sci. USA 64: 600 (1969), John et al., Nature (London) 223: 582 (1969), Rudkin and Stollar, Nature (London) 265: 472 (1977)).

A large variety of hybridization probes, comprised of DNA and RNA sequences, are known in the art.

Gall and Pardue, supra, disclose the use of complementary RNA (cRNA) probes labeled with tritium-containing nucleotides for the detection of specific sequences on lampbrush chromosomes.

John et al., supra, disclose the use of cRNA probes labeled with $^{125}I$ to detect DNA:RNA hybrids.

Bauman et al., Exp. Cell Res. 128: 485-490 (1980) discloses detection of ribosomal 5S genes on polytene chromosomes in D. hydei after hybridization to labeled 5S RNA.

Malcolm et al., Ann. Hum. Genet. 45: 135-142 (1981) disclose the detection of the human B-globin gene on chromosome 11 after in situ hybridization of normal human chromosomes with a labeled complementary DNA (cDNA) probe.

Manuelidis et al., J. Cell Biol. 95: 619-625 (1982) disclose detection of mouse satellite DNA sequences in mouse chromosomes after hybridization with a labeled mouse satellite-specific DNA probe.

Landegent et al., Exp. Cell Res. 153: 61-72 (1984) disclose detection of mouse chromosomes after hybridization with cloned satellite DNA sequences.

Landegent et al., Nature (London) 317: 175-177 (1985) disclose detection of the human thyroglobulin gene at a specific chromosomal location after hybridization with labeled cosmid clone DNA.

Hopman et al., Histochemistry 85: 1-4 (1986) disclose detection of human chromosomes in mouse:human somatic cell hybrids after hybridization with labeled total human DNA and detection of mouse chromosomes after hybridization with cloned mouse satellite DNA sequences.

Landegent et al., Hum Genet. 73: 354-357 (1986) disclose the detection of a specific portion of human chromosome 4 after hybridization with a cloned genomic DNA probe, which has been genetically linked to the gene for Huntington's disease.

Moyzis et al., Chromosoma (Berlin) 95: 375-386 (1987) disclose specific detection of portions of human chromosomes 9 and 16 after hybridization with cloned human satellite DNA probes.

van Dekken and Bauman, Cytogenet. Cell Genet. 48: 188-9 (1988) disclose specific detection of human chromosome 1 after hybridization with fluorescently labeled cloned probes specific for the repetitive sequences found at the centromere and telomere.

Emmerich et al., Exp. Cell Res. 181: 126-140 (1989) disclose specific detection of human chromosomes 1 and 15 after hybridization with cloned probes to tandemly repeated human DNA.

Pieters et al., Cytogenet. Cell Genet. 53: 15-19 (1990) disclose detection of human chromosomes in individual sperm cells after hybridization with labeled chromosome-specific probes.

van Dekken et al., Cytometry 11: 153-164 (1990) disclose detection by flow cytometry of chromosomes 1 and Y in interphase and metaphase nuclei of normal human blood cells after hybridization with chromosome-specific labeled DNA probes.

Cremer et al., Cytometry 11: 110-118 (1990) disclose the detection of specific chromosomal damage induced by treatment of human peripheral lymphocytes with ionizing radiation after hybridization with labeled chromosome-specific DNA probes.

Kievits et al., Cytometry 11: 105-109 (1990) disclose the detection in human lymphocyte preparations of specific chromosomes or portions of chromosomes after hybridization with labeled total genomic DNA of mouse:human somatic cell hybrids and after pretreatment of the labeled DNA with unlabeled total human genomic DNA.

Methods for labeling DNA and RNA probes are well known in the art. These methods include enzymatic incorporation of modified nucleotides, chemical synthesis of probes containing modified nucleotides and direct modification of nucleotides. The modifications include derivatization of nucleotides for the addition of labels or haptens, and the direct addition of labels or happens. Traditional methods involved the incorporation of radioactive isotopes such as $^3H$, $^{14}C$, $^{35}S$, $^{32}P$ and $^{125}I$. The inherent instability and correspondingly short useful lifetime of probes incorporating radioactive label, as well as health and waste management concerns, have prompted the adoption of a number of nonradioactive compounds for labeling probe DNA and RNA.

U.S. Pat. No. 4,833,251 discloses direct and synthetic modification of DNA probes, and teaches derivatization of DNA as an N[4] (substituted amino) cytosine. This derivatization is taught by incorporation of derivatized nucleotides into DNA synthesized enzymatically or by solid-phase chemistry. Derivatization is also taught by direct modification of single stranded DNA prepared from genomic eukaryotic DNA and from DNA cloned in prokaryotes using techniques well known to the skilled.

U.S. Pat. No. 4,828,979 discloses biotin modification of nitrogen atoms at nucleotide bases, which are involved in Watson-Crick base pairing of hybridized DNA and RNA sequences, and teaches the synthesis of probes labeled with biotin at these positions.

U.S. Pat. No. 4,626,501 teaches the derivatization of DNA and RNA sequences at adenosine and cytosine residues by conjugation of these residues at nitrogen atom positions N-6 and N-4, respectively, with the compound 3-(4-bromo-3-oxobutane 1-sulfonyl)-propionate and a number of related compounds.

Dale et al., Biochemistry 14: 2447–2457 (1975) teach the derivatization of nucleotides and polynucleotides with mercurated compounds.

Bauman et al., Exp. Cell Res. 128: 485–490 (1980) teach the chemical conjugation of fluorescent compounds directly to the 3' hydroxyl moiety of RNA molecules after treatment with sodium periodate.

Langer et al., Proc. Natl. Acad. Sci. USA 78: 6633–6637 (1981) disclose the enzymatic incorporation into probe DNA and RNA of UTP and dUTP that has been modified at the carbon atom 5 (C-5) position of the nucleotide.

Renz, EMBO J. 2: 817–822 (1983) teaches the conjugation of single stranded DNA probes with biotin or $^{125}$I labeled histone H1 protein.

Tchen et al., Proc. Natl. Acad. Sci. USA 81: 3466–3470 (1984) disclose addition of the hapten 2-acetylaminofluorene to single stranded and double stranded DNA and RNA probes specifically at guanosine nucleotides.

Landegent et al., Exp. Cell Res. 153: 61–72 (1984) teach the use of 2-acetylaminofluorene labeled mouse satellite DNA probes for the in situ detection of mouse chromosomes.

Draper, Nucleic Acids Res. 12: 989–1002 (1984) teaches the derivatization of polynucleotides by bisulfite-catalyzed transamination and discloses the labeling of derivatized polynucleotides with a fluorescent compound, nitrobenzofurazan.

Forster et al., Nucleic Acids Res. 13: 745–761 (1985) disclose labeling of DNA and RNA photochemically with a photoactive derivative of biotin.

Hopman et al., Histochemistry 85: 1–4 (1986) disclose the use of mercurated human total genomic DNA probes for in situ detection of human chromosomes.

The use of 2,4-dinitrophenyl labels for labeling DNA is well known in the prior art.

U.S. Pat. No. 4,948,882 teaches the use of DNP-labeled DNA probes prepared by nick translation using deoxynucleotide triphosphates linked to the DNP label via diaminoalkyl linker arms.

U.S. Pat. No. 4,898,951 teaches direct labeling of DNA with a photoactive derivative of DNP.

U.S. Pat. No. 4,876,395 teaches labeling of synthetic oligonucleotide probes at the 5' terminal hydroxyl with DNP via a poly-lysine linking group.

U.S. Pat. No. 4,849,336 teaches labeling of synthetic oligonucleotide probes at the 5' terminal hydroxyl with DNP via straight chain or branched chain hydrocarbon linking groups.

U.S. Pat. No. 4,833,251 teaches the use of DNP-labeled DNA probes prepared by nick translation using deoxynucleotide triphosphates linked to the DNP label via diaminoalkyl linker arms and labeled specifically at cytosine residues.

U.S. Pat. No. 4,626,501 teaches the labeling of DNA probes with DNP-lysine via a linker arm which is 3-(4-bromo-3-oxobutane-1-sulfonyl)-proprionate N-hydroxysuccinimidyl ester.

Vincent et al., Nucleic Acids Res. 10: 6787–6796 (1982) teach the preparation of 8-(2,4-dinitrophenyl-2,6-diaminohexyl)-amino adenosine 5' triphosphate and its use for end labeling DNA probes.

Shroyer and Nakane, J. Cell Biol. 97: Abstract 377a (1983) disclose the derivatization of cDNA probes by treatment with dinitrophenol.

Hopman et al., Nucleic Acids Res. 16: 6471–6488 (1986) teach the use of trinitrophenyl-lysine-B-mercaptoethanol ligand to label mercurated DNA.

Moriuchi et al., Nucleic Acids Res. Symp. Ser. 19: 77–80 (1988) teach the end-labeling of DNA by reaction with 2,4-dinitrobenzaldehyde under alkaline conditions.

Keller et al., Anal. Biochem. 170: 441–450 (1988) teach the labeling of brominated DNA with 6-(2,4-dinitrophenylamino)-1-aminohexane.

Keller et al., Anal. Biochem. 177; 392–395 (1989) teach the labeling of alkali-nicked DNA with a photoactivatable derivative of DNP, 6-(2,4-dinitrophenylamino)-1-aminohexyl-6'-(4'-azido-2'-nitrophenylamino) hexanoate.

Singh et al., Nucleic Acids Res. 18: 3339–3345 (1990) teach the preparation of ω-DNP-alkyl-amino-labeled oligonucleotides.

Lichter et al., Science 247: 64–69 (1990) teach the use of DNP-labeled DNA probes prepared by nick translation using 5-(3-amino) allyl-dUTP.

A number of methods well known in the art have been developed for the detection of non-radioactively labeled probes. These methods include direct detection of fluorescently labeled compounds, and indirect methods, which rely on the binding of a reporter molecule that is then detected either directly or indirectly. These reporter-based methods include immunological methods, in which antibodies recognize either the target:-probe hybrid molecule itself or the hapten derivatized to the probe, and affinity methods, which are based on specific interactions with hapten molecules derivatized to the probe. Detection of these reporter molecules has been achieved by the attachment of a fluorescent label, conjugation to an enzyme followed by enzymatic conversion of its substrate to a detectable product, or conjugation with electron-dense atoms, such as gold, iron or silver, and detection either visually or by electron microscopy.

Manning et al., Chromosoma 53: 107–117 (1975) disclose that biotin, covalently attached to RNA via electrostatic interaction between RNA and cytochrome c, can be detected after in situ hybridization by binding of ferritin-conjugated avidin molecules and visualization by electron microscopy.

Rudkin and Stollar, Nature (London) 317: 472–473 disclose detection of in situ hybridization by the use of fluorescently labeled antibodies against RNA:DNA hybrids.

Hutchinson et al., J. Cell Biol. 95: 609–618 (1982) disclose the use of avidin conjugated with colloidal gold to detect in situ hybridization of biotinylated probes by electron microscopy.

Manuelidis et al., J. Cell Biol. 95: 619–625 (1982) disclose the use of fluorescently labeled antibodies to detect in situ hybridization with biotinylated mouse satellite DNA probes.

Shroyer and Nakane, supra, disclose directly labeling cDNA clones with dinitrophenol and use of these probes for in situ hybridization of albumin messenger RNA.

Landegent et al., Hum. Genet. 73: 354–357 (1986) disclose the use of horseradish peroxidase-conjugated antibodies to detect in situ hybridization of a 2-acetylaminofluorene-conjugated cosmid probe for a Huntington's disease gene.

Hopman et al., Histochemistry 84: 169–178 (1986) disclose the use of sulfhydryl happens to mercurated DNA probes for the immunological detection of in situ hybridization. Hopman et al., Nucleic Acids Res. 14: 6471–6488 (1986) teach the use of trinitrophenyl haptens derivatized to sulfhydryl-containing linker molecules for the detection of in situ hybridized, mercurated probe DNA.

Garson et al., Nucleic Acids Res. 15: 4761–4770 (1987) disclose the use of streptavidin conjugated with alkaline phosphatase to detect hybridization of biotinylated probes for the human N-myc and B-NGF genes.

Moriuchi et al., supra, disclose the use of directly DNP-labeled cDNA probes for the in situ detection of c-myc and T-cell receptor B chain gene expression and infection of HTLV-I in human adult T-cell leukemia cells.

Keller et al., supra, teach the use of DNA labeled with 6-(2,4-dinitrophenylamino)-1-aminohexane to detect Hepatitis virus sequences immobilized on nitrocellulose.

Keller et al., supra, teach the use of DNA labeled with 6-(2,4-dinitrophenylamino)-1-aminohexyl-6'-(4'-azido-2'-nitrophenylamino) hexanoate, to detect Human Immune Deficiency Virus (HIV) immobilized on nitrocellulose.

Lichter et al., supra, teach in situ hybridization using cosmid clones labeled with dinitrophenyl (DNP) by nick-translation with DNP-labeled dUTP.

The prior art contains examples of a variety of enzymatic and chemical methods for labeling and derivatizing nucleic acid probes. Such probes can be detected by a large number of direct and indirect detection systems. Specifically, the prior art contains examples of DNA labeling with dinitrophenyl and detection of this labeled DNA by immunological means. However, a number of experimental limitations on the use of DNP are found in the prior art, including limited solubility of DNP-labeled DNA and reduced sensitivity of detection of directly and internally DNP-labeled DNA. This invention relates to methods and compounds for labeling DNA with multiple labels comprising phenyl substituted with one to three nitro groups, said labels covalently linked thereto by means of an amino acid linking group. The reagents and methods of synthesizing these labeled DNAs overcome the limitations associated with the use of nitro-substituted phenyl labels known in the prior art. These reagents permit the in situ detection of chromosomes or regions of chromosomes. The nitro-substituted phenyl labels bound to the chromosome, region of chromosome or other target can conveniently be detected by immunological techniques.

SUMMARY OF THE INVENTION

Figure 1:
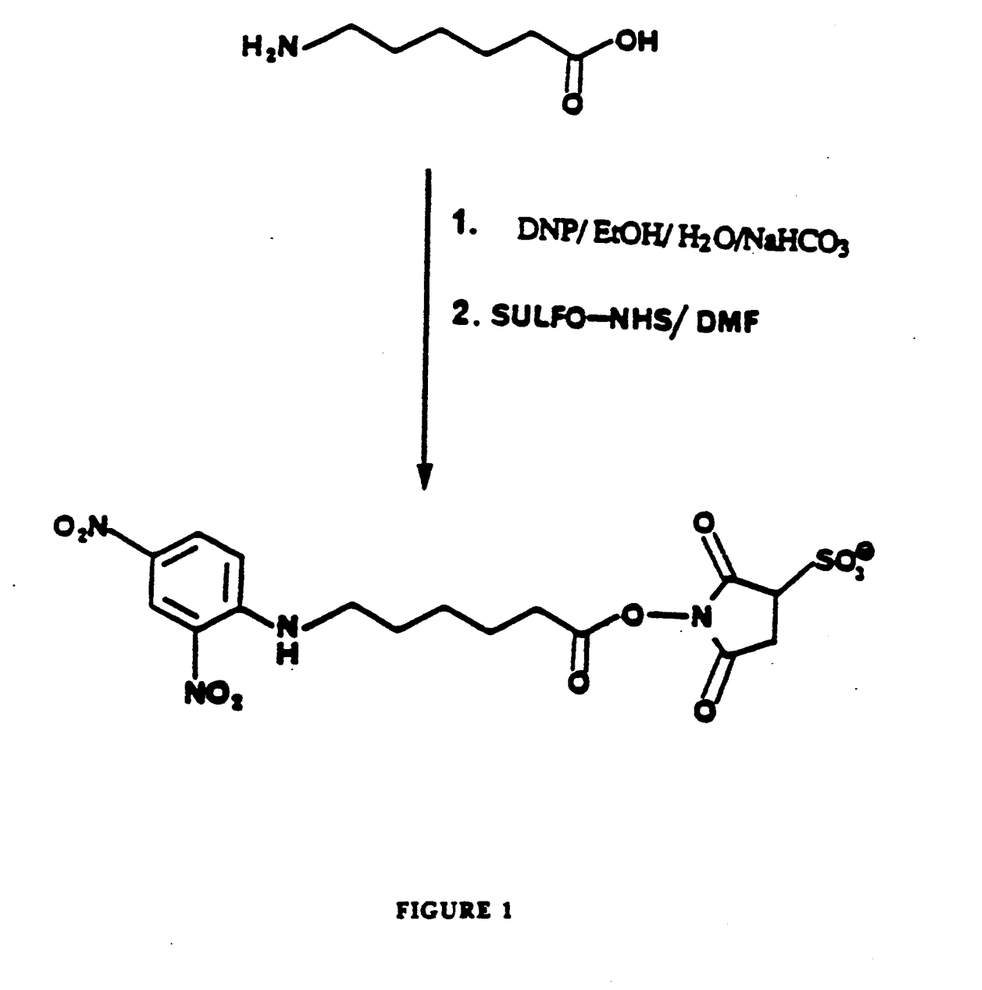
FIG. 1 illustrates the preparation of 6-N-(2,4-dinitrophenyl) caproic acid-O-(N-hydroxysuccinimidyl-3-sulfonate) ester.
Figure 2:
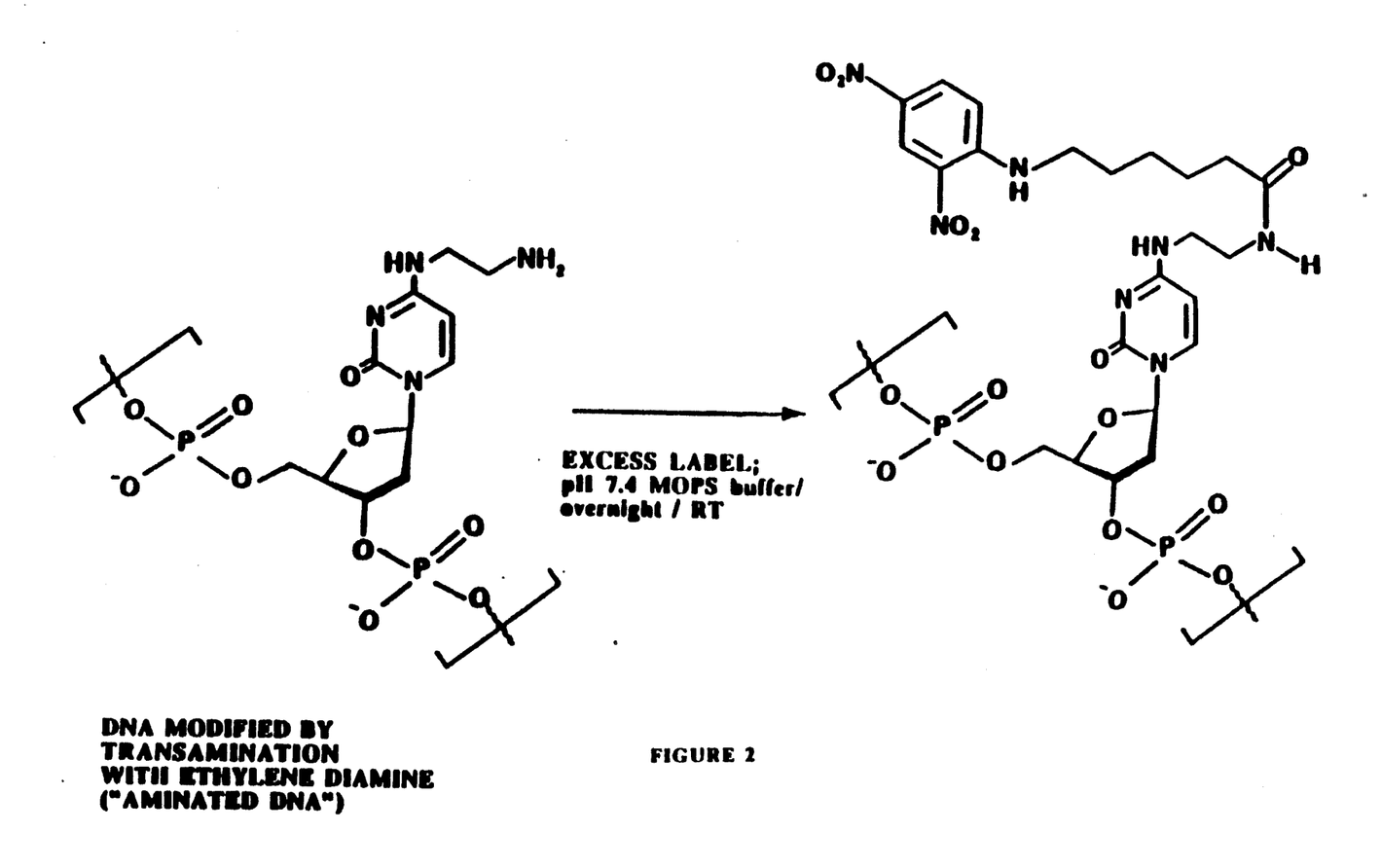
FIG. 2 illustrates reaction of 6-N-(2,4-dinitrophenyl) caproic acid-O-(N-hydroxysuccinimidyl-3-sulfonate) ester with DNA that has been transaminated with ethylenediamine.

It is an object of the present invention to provide: 1. methods and compounds for labeling DNA with multiple labels comprising phenyl substituted with one to three nitro groups, said labels covalently linked thereto by means of an amino acid linking group, 2. reagents for the in situ detection of a chromosome or region of a chromosome, 3. methods for the preparation of such reagents and 4. methods for the use of such reagents for the in situ detection of a chromosome or region of a chromosome.

This invention provides methods and compounds for covalently binding an antigenic label to DNA, as well as the antigen-labeled DNA, wherein the antigenic moiety of the label is nitrosubstituted phenyl, which is covalently linked to the DNA. The nature of the covalent linkage is by means of an amino acid linking group. For the purposes of the present invention, an amino acid linking group is defined as being comprised of compounds of the formula I:

wherein $R_1$ and $R_2$ are independently hydrogen or alkyl or aryl substituents, preferably hydrogen, and $n=1-6$. Preferred linker arms ar derivatives of simple lower alkyl amino acids (wherein $R_1$ and $R_2$ are hydrogen), including but not limited to formic, acetic, proprionic, butyric, valeric and caproic acid derivatives, natural and synthetic L-amino acids, and polymers and copolymers thereof. The most preferred labels are the 2,4-dinitrophenyl derivatives of ε-amino-n-caproic acid and glycylglycylglycine.

This invention provides a reagent for in situ detection of nucleic acid sequences comprising one or more DNA sequences complementary to the nucleic acid to be detected wherein the DNA sequences include multiple labels comprising phenyl substituted with one to three nitro groups, said labels covalently linked thereto by means of an amino acid linking group. The preferred labels are the 2,4-dinitrophenyl derivatives of ε-amino-n-caproic acid and glycylglycylglycine.

The invention includes a reagent for in situ detection of a chromosome or region of a chromosome comprising unhybridized DNA sequences having essentially complementary base sequences with respect to different portions of the chromosome or chromosome region to be detected and having a plurality of cytosine bases that are transaminated, a number of the transaminated cytosine bases having a nitro-substituted phenyl label covalently bonded thereto, the number of said nitro-substituted phenyl labeled cytosine bases being sufficient for detection by immunological techniques while essentially retaining the specific binding properties of the reagent with respect to the chromosome or chromosome region to be detected.

The invention also includes a method for making a reagent for in situ detection of a chromosome comprising:
(a) disrupting plasmid DNA containing DNA complementary to the chromosome or region of chromosome to be detected into fragments,
(b) transaminating the DNA fragments, and
(c) covalently linking nitro-substituted phenyl labels to the transaminated DNA by means of an amino acid linking group.

More specifically, the invention includes a method for preparing a reagent for in situ detection of a chromosome or region of a chromosome comprising:
(a) transaminating a number of cytosine bases contained in unhybridized DNA sequences having essentially complementary base sequences with respect to the chromosome or chromosome region to be detected; and
(b) covalently bonding multiple labels comprising phenyl substituted with one to three nitro groups, said labels covalently linked thereto by means of an amino acid linking group to at least a portion of the transaminated cytosine bases, the portion of cytosine bases having nitro-substituted phenyl labels covalently bonded thereto being sufficient to generate a detectable nitro-substituted phenyl signal while essentially retaining the specific binding properties of the reagent with respect to the chromosome or chromosome region to be detected.

In addition the invention provides a method for in situ detection of a chromosome or region of a chromosome comprising:
(a) adding an excess of blocking DNA to the inventive reagent under hybridizing conditions to bond with nonspecific binding DNA in the reagent, thereby forming a blocked reagent,
(b) contacting the blocked reagent under hybridizing conditions with the chromosome or chromosome region to be detected, and
(c) detecting the binding of the blocked reagent to the chromosome or chromosome region to be detected by immunological techniques.

It is an additional object of the present invention to provide as a reagent DNA covalently labeled with nitro-substituted phenyl label. It is a specific object of the present invention to provide a reagent for the in situ detection of a chromosome or region of a chromosome wherein the reagent contains multiple DNA sequences that are complementary to different portions of the chromosome or chromosome region to be detected. The multiple DNA sequences in the reagent include multiple labels comprising phenyl substituted with one to three nitro groups, preferably 2,4-dinitrophenyl labels that are covalently linked to the DNA sequences by means of an amino acid linking group. These nitro-substituted phenyl, preferably 2,4-dinitrophenyl labels permit the DNA sequences that hybridize with the chromosome or chromosome region of interest to be detected using immunological techniques. The nitro-substituted phenyl, preferably 2,4-dinitrophenyl labels are covalently linked to any of the bases adenosine, guanosine, cytosine or thymidine comprising the DNA sequences. In a preferred embodiment, the nitro-substituted phenyl, preferably 2,4-dinitrophenyl labels are covalently linked to a number of transaminated cytosine bases in the DNA sequences. The number of transaminated cytosine bases having nitro-substituted phenyl, preferably 2,4-dinitrophenyl labels is sufficient to provide an amount of nitro-substituted phenyl, preferably 2,4-dinitrophenyl labels to be detectable by immunological techniques, while at the same time essentially retaining the specific binding properties of the DNA sequences with respect to the chromosome or chromosome region of interest.

It is an additional specific object of the present invention to provide methods for making reagents for the in situ detection of a chromosome or region of a chromosome. The first step of a preferred method is to disrupt plasmid DNA derived from a phage chromosomal library into fragments. These DNA fragments are transaminated and functional derivatives of multiple labels comprising phenyl substituted with one to three nitro groups, preferably 2,4-dinitrophenyl labels, covalently linked thereto by means of an amino acid linking group, are then covalently linked to the transaminated DNA fragments. In the present invention, the number of transaminated cytosine bases to which nitro-substituted phenyl, preferably 2,4-dinitrophenyl labels are covalently bonded is sufficient to generate a immunologically detectable amount of nitro-substituted phenyl, preferably 2,4-dinitrophenyl labels while at the same time essentially retaining the specific binding properties of the reagent with respect to the chromosome or chromosome region to be detected.

It is a further specific object of the present invention to provide methods for the in situ detection of a chromosome or region of a chromosome. In general, the preferred methods are carried out by contacting the reagents of the present invention with the chromosome or chromosome region to be detected under hybridization conditions.

It is an additional object of the present invention to provide methods for the detection of any nucleic acid sequence complementary to DNA covalently labeled with nitro-substituted phenyl, preferably 2,4-dinitrophenyl. The nitro-substituted phenyl, preferably 2,4-dinitrophenyl labels allow the introduction of a reporter molecule, such as a fluorescent or enzyme labeled antibody, to any probe-target complex. The target may be chromosomal DNA, but may additionally be RNA, such as messenger or ribosomal RNA; extrachromosomal DNA, such as mitochondrial DNA; or prokaryotic DNA, such as bacterial or viral DNA. The DNA probe assay may involve in situ hybridization, solution phase hybridization, hybridization to nucleic acids immobilized on a solid phase, or hybridization to blots of nucleic acid or protein immobilized on any of a number of transfer media, including but not limited to nitrocellulose, nylon and other synthetic derivatives known in the art.

The presence of the nitro-substituted phenyl, preferably 2,4-dinitrophenyl labels is detected by immunological techniques. Nitro-substituted phenyl labels are haptens against which antibodies can be raised. For example, an anti-dinitrophenyl antibody is reacted with the 2,4-dinitrophenyl moiety of the reagent bound to the target chromosome. A second antibody specifically reactive to the anti-dinitrophenyl antibody and which is labeled with an enzyme or fluorescent marker is then bound to the anti-dinitrophenyl antibody to indirectly determine the binding of the 2,4-dinitrophenyl containing DNA to the chromosome. Those skilled in the immunological arts recognize a large number of techniques for immunologically determining the presence of a hapten such as 2,4-dinitrophenyl.

In a preferred embodiment, an excess of blocking DNA is added to the reagent under hybridizing conditions. This blocking DNA then binds with any nonspecific binding DNA in the reagent, thereby forming a blocked reagent. This blocked reagent can then be contacted with the chromosome or chromosome region of interest under hybridizing conditions.

The present invention additionally includes a reagent comprising DNA having one or more labels comprising phenyl substituted with one to three nitro groups, covalently linked thereto by means of an amino acid linking group and wherein the nitro substituted phenyl label is detectable by immunological techniques and the DNA retains its binding properties.

The present invention also includes a compound which is is 6-N-(2,4-dinitrophenyl) caproic acid-O-(N-hydroxysuccinimidyl-3-sulfonate) ester.

The present invention also includes a compound which is N-(2,4-dinitrophenyl) glycylglycylglycine-O-(N-hydroxysuccinimidyl-3-sulfonate) ester.

The present invention also includes a reagent for in situ detection of nucleic acid sequences comprising one or more DNA sequences complementary to the nucleic acid to be detected wherein the DNA sequences include multiple dinitrophenyl labels covalently bound to DNA by means of activated derivatives of $\epsilon$-amino-n-caproic acid and glycylglycylglycine.

The present invention also includes a method for preparing a reagent for labeling DNA comprising:
(a) reacting an amino acid linking group with labels comprising phenyl substituted with one to three nitro groups so as to form a covalent linkage;
(b) activating the resulting label-linker compound by esterification to 3-sulfo-N-hydroxysuccinimide; and
(c) covalently bonding the activated label-linker compound to transaminated DNA.

In a preferred embodiment, Sanger's reagent (2,4-dinitrofluorobenzene) is reacted with $\epsilon$-amino-n-caproic acid to form 6-(-2,4-dinitroamino)caproic acid. This compound is then esterified by reaction with 3-sulfo-N-hydroxysuccinimide to form the activated ester. This activated ester is then used to label transaminated DNA. In another preferred embodiment, the amino terminus of the tripeptide glycylglycylglycine is reacted with Sanger's reagent to form the (2,4-dinitroamino)-glycylglycylglycine. This compound is then esterified by reaction with 3-sulfo-N-hydroxysuccinimide to form the activated ester. This activated ester is then used to label transaminated DNA.

Further objects and preferred embodiments of the present invention will be discussed in the following description of the preferred embodiments and claims.

DETAILED DESCRIPTION OF THE PREFERRED EMBODIMENTS

This invention encompasses methods and compounds for labeling DNA with labels comprising phenyl substituted with one to three nitro groups covalently linked thereto by means of an amino acid linking group, and reagents and methods for the in situ identification of chromosomes or regions of chromosomes. The invention encompasses a reagent comprising a multiplicity of DNA sequences complementary to different portions of the chromosome or chromosome regions to be detected wherein the DNA sequences are aminated at multiple sites and labeled with nitro-substituted phenyl labels at the aminated sites by covalent linkage of a functionalized derivative of an amino acid linking group.

The sources of the DNA sequence used in the invention include but are not limited to DNA isolated from specific chromosomes, or libraries of such DNA, prepared by methods well known to those with skill in the art. The individual chromosomes from which DNA is isolated can be prepared by any of a number of standard methods, such as flow cytometry of microcell or somatic cell hybrids, or by direct isolation from individual metaphase or interphase cells. Another source of such DNAs are libraries of specific chromosomal DNA, prepared by standard methods and available from traditional sources known to those in the art, such as the American Type Culture Collection (ATCC) or other repositories of human or, other cloned genetic material. While a large number of chromosome libraries are available from the ATCC, representative libraries are:

| Human Chromosome Library | ATCC No. |
| --- | --- |
| 1 | 57738 |
| 1 | 57753 |
| 1 | 57754 |
| 2 | 57716 |
| 2 | 57744 |
| 3 | 57717 |
| 3 | 57748 |
| 3 | 57751 |
| 4 | 57719 |
| 4 | 57718 |
| 4 | 57700 |
| 4 | 57745 |
| 5 | 57720 |
| 5 | 57746 |
| 6 | 57721 |
| 6 | 57701 |
| 7 | 57722 |
| 7 | 57755 |
| 8 | 57723 |
| 8 | 57702 |
| 9 | 57724 |
| 9 | 57705 |
| 10 | 57725 |
| 10 | 57736 |
| 11 | 57726 |
| 11 | 57704 |
| 12 | 57727 |
| 12 | 57736 |
| 13 | 57728 |
| 13 | 57705 |
| 14 | 57739 |
| 14 | 57706 |
| 14/15 | 57707 |
| 15 | 57729 |
| 15 | 57740 |
| 15 | 57737 |
| 16 | 57765 |
| 16 | 57730 |
| 16 | 57749 |
| 16 | 57758 |
| 17 | 57741 |
| 17 | 57759 |
| 18 | 57742 |
| 18 | 57710 |
| 19 | 57731 |
| 19 | 57766 |
| 19 | 57711 |
| 20 | 57732 |
| 20 | 57712 |
| 21 | 57743 |
| 21 | 57713 |
| 22 | 57733 |
| 22 | 57714 |
| X | 57750 |
| X | 57734 |

-continued

| Human Chromosome Library | ATCC No. |
|---|---|
| X | 57752 |
| X | 57747 |
| Y | 57735 |
| Y | 57715 |

The ATCC deposits are available from the American Type Culture Collection, 12301 Parklawn Drive, Rockville, Md. The invention contemplates that such DNA sequences may also be synthesized in vitro by any of a number of enzymatic means known to those in the art. Also see an article entitled Human Chromosome-Specific DNA Libraries, Biotechnology 4: 537 (1986), which describes the preparation of human chromosome libraries.

DNA used in the invention is isolated from these sources by methods which are well known to those skilled in the art. This DNA is then reduced to a heterogenous mixture of variably sized fragments by any of a number of physical, chemical or enzymatic treatments, including but not limited to sonication, limited DNase I digestion, limited mung bean nuclease digestion, and shearing of DNA through a narrow-gauge needle. The resulting mixture of DNA fragments will be within a size range of 100-500 basepairs (bps) in length, although the preferred length of the average size of a fragment is about 300 bps. These procedures provide a large number of DNA sequences complementary to different portions of the chromosomes to be detected. In fact thousands if not tens of thousands of DNA sequences complementary to different portions of the chromosome DNA are provided.

The DNA fragments are derivatized by any of a number of chemical means known to those in the art, preferrably by transamination of the carbon 4 (C-4) atom amino group of the nucleotide base cytosine. The derivatization will result in the addition of a variety of diamine compounds at the C-4 position in this base, including but not limited to such compounds as hydrazine and alkylene diamines having 2 to 10 carbon atoms such as ethylenediamine, amino acids, peptides, ether derivatives, or any of a number of other organic or inorganic linker molecules. The DNA fragments have 5-25% of the cytosine residues contained therein transaminated, with an optimum transamination of 20%. About 3-6% of the total nucleotide residues are transaminated, with an optimum of 5% of the total bases transaminated.

The transaminated DNA sequences are covalently linked to any of a number of labels comprising phenyl substituted with one to three nitro groups covalently linked thereto by means of an amino acid linking group, and which have a functional group capable of covalent bond formation with the transaminated DNA sequence. Preferred compounds that can be used to label the transaminated DNA sequences with dinitrophenol (DNP) are 6-N-(2,4-dinitrophenyl) caproic acid-O-(N-hydroxysuccinimidyl-3-sulfonate) ester or N-(2,4-dinitrophenyl) glycylglycylglycine-O-(N-hydroxysuccinimidyl-3-sulfonate) ester. The transaminated DNA sequences are reacted with a 100-200-fold molar excess of functionalized DNP compound, preferably about a 150-fold molar excess. 60-80% of transaminated sites are labeled, preferably 2,4-dinitrophenyl-labeled.

DNA sequences which are labeled with multiple labels comprising phenyl substituted with one to three nitro groups covalently linked thereto by means of an amino acid linking group are used for in situ hybridization to target chromosomes. For the purposes of this invention "in situ" means that the chromosomes are exposed from the cell nucleus without substantial disruption or relocation of the chromosomes with respect to each other and with the chromosomes being accessible to the nitro-substituted phenyl, preferably 2,4-dinitrophenyl-labeled DNA probes. Targets for this hybridization include but are not limited to chromosomes or regions of chromosomes in normal, diseased or malignant human or other animal or plant cells, either interphase or at any stage of meiosis or mitosis, and either extracted or derived from living or postmortem tissues, organs or fluids; germinal cells including sperm and egg cells, seeds, pollen, or zygotes, embryos, chorionic or amniotic cells, or cells from any other germinating body; cells grown in vitro, from either long-term or short-term culture, and either normal, immortalized or transformed; inter- or intraspecific hybrids of different types of cells or differentiation states of these cells; individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to semen, blood, hair or other samples.

Prior to hybridization, the labeled DNA sequences are reacted with an excess of corresponding unlabeled DNA or reassociated fraction of unlabeled DNA to bind with nonspecific binding DNA in the sample, thereby blocking the nonspecific DNA to provide a blocked reagent. This blocking DNA is used at a concentration of 1-10 micrograins per 10 microliters of total genomic DNA, with a preferred range depending on the hybridized chromosome of between 2.25 and 6.75 micrograms per 10 microliters, or between 1 and 4 micrograms per 10 microliters, preferably about 1.3 micrograms per 10 microliters. The blocking DNA may be human placental DNA or Cot1 DNA (Cot1 DNA supplied by Life Technologies, Gaithersburg, Md., Cat. #5279SA) is prepared by mechanically shearing total human genomic DNA to an average size of less than 400 base pairs. This material is denatured and then rehybridized for a period sufficient to render a large fraction of the highly repeated DNA sequences double-stranded. The mixture of double and single-stranded DNA species are treated with nuclease S1, a nuclease that specifically degrades single-stranded DNA to mono- and oligo-nucleotides. Undigested, double stranded Cot1 DNA is recovered from this mixture.

Chromosomes are then preferably stained so as to be visible with an)r of a number of counterstains, including but not limited to propidium iodide, quinacrine, or distamycin/4,6-diamino-2-phenylindole (DAPI) or with a non-fluorescent dye such as Giemsa. These counterstains permit visualization of all of the chromosomes.

Thus this invention provides a mixture of a large number of DNA sequences which include multiple labels comprising phenyl substituted with one to three nitro groups covalently linked thereto by means of an amino acid linking group, preferably 2,4-dinitrophenyl-labeled DNA sequences, that are complementary to different portions of the chromosomes to be detected. The methods of this invention provide thousands, if not tens of thousands of different DNA sequences that are complementary to the chromosome being detected and are labeled with nitro-substituted phenyl, most preferably 2,4-dinitrophenyl labels. Hybridization of this large number of different labeled DNA sequences to a substantial portion of the chromosomes permits detection of the chromosome by reacting the hybridized, labeled DNA with an antibody against the label and in turn binding the antibody bound to the label with an antibody labeled with an enzyme or fluorescent marker and which is specific for the antibody bound to the label. Those skilled in the immunological arts will recognize a large number of immunological techniques by which the nitro-substituted phenyl, most preferably 2,4-dinitrophenyl labels can be detected. Nitro-substituted phenyl labels are haptens against which antibodies are raised by well known techniques. Techniques for labeling antibodies with fluorescent markers such as fluorescein, rhodamine and the like are well known. It is also well known to label antibodies with enzymes such as horseradish peroxidase and alkaline phosphatase. For example, the 2,4-dinitrophenyl label on the DNA fragments hybridized to the target chromosome could be detected by reaction directly with a fluorescent or enzyme labeled anti-DNP antibody. The complex is represented as follows:

Chromosome DNA/complementary DNA-2,4-dinitrophenyl labeled/anti-DNP antibody (fluorescent or enzyme label)

In another configuration, the 2,4-dinitrophenyl label is reacted with an anti-DNP antibody, which in turn is bound to an antibody against the anti-DNP antibody that has a fluorescent or enzyme label. For example, rabbit anti-DNP antibody is first bound to the DNP label and is followed by goat anti-rabbit antibody that has a fluorescent or enzyme label. This configuration is represented as follows:

Chromosome DNA/complementary DNA-2,4-dinitrophenyl labeled/rabbit anti-DNP antibody/goat anti-rabbit antibody (fluorescent or enzyme labeled)

The fluorescent or enzyme labels are detected by standard techniques. Those skilled in the immunological arts will recognize a large number of assay configurations, fluorescent labels, and enzyme labels for detecting haptens such as nitro-substituted phenyl, particularly 2,4-dinitrophenyl. Advantage may also be taken of other specific binding substances such as avidin/biotin in configuring assays for nitro-substituted phenyl, particularly 2,4-dinitrophenyl label.

The present invention is further illustrated by the following examples. However, many embodiments not specifically described herein nevertheless fall within the spirit and scope of the present invention.

EXAMPLE 1

Isolation of Human Chromosome-Specific DNA Probes

Human chromosome-specific DNA probes were obtained as recombinant phage libraries from Lawrence Livermore National Laboratories (LLNL) constructed as described in Van Dilla, M. A. et al. (Biotechnology 4: 537-552, 1986). These libraries were amplified by growth on an $E.$ $coli$ host strain. The amplified phage were purified, their DNA was extracted, and this DNA was digested with the restriction enzyme Hind III. Insert DNA was purified away from the lamda vector DNA and cloned into the Hind III site of the plasmid vector pBS (Strategene, La Jolla, Calif.). The resulting plasmids were transformed into an $E.$ $coli$ strain, DH5α (Bethesda Research Libraries, Gaithersburg, Md.).

The plasmid libraries exemplified herein are ATCC #'s 57738, 57753 and 57754 (Chromosome 1) ; ATCC numbers 57749, 57748, and 57751 (Chromosome 3); ATCC numbers 57723 and 57702 (Chromosome 8) and ATCC numbers 57727 and 57736 (Chromosome 12). The libraries are stored as 1 ml aliquots of frozen cells. These vials have been used as the primary source for the production of seed stocks for fermentation.

Bacteria were grown by fermentation. The seed stock obtained from ATCC was cultured at 37° C. for 24 hr. on 1.6% agar plates containing ampicillin (200 microgram/ml) and YT broth, which contains 8 grams per liter (g/l) of Bacto Tryptone (Difco), 5 g/l of Bacto Yeast Extract (Difco), 15 g/l of Bacto Agar (Difco), and 5 g/l of sodium chloride. The cultured cells were harvested with 4 ml containing 16 g/l of Bacto Tryptone (Difco), 10 g/l of Bacto Yeast Extract (Difco) and 5 g/l of sodium chloride, and 4 ml of 20% glycerol was added to each harvest. The $E.$ $coli$ cell culture was quickly frozen in 0.5 ml aliquots by submerging the vials in liquid nitrogen and stored at −80° C. until use.

The fermenter inoculum was prepared in 350 ml by culturing the seed culture in a Casamino Acid medium which contains 13.2 g/l $Na_2HPO_4-7H_2O$, 3.0 g/l $KH_2PO_4$, 0.05 g/l NaCl, 1.0 g/l $NH_4Cl$, 10.0 g/l Casamino Acids (Difco); 0.03 g/l $MgSO_4$, 0.004 g/l $CaCl_2-2H_2O$, 3.0 g/l glucose, 0.025 g/l Thiamine-HCl, 0.0054 g/l $FeCl_3$, 0.0004 g/l $ZnSO_4$, 0.0007 g/l $COCl_2$, 0.0007 g/l $Na_2MoO_4$, 0.0008 g/l $CuSO_4$, 0.0002 g/l $H_2BO_3$, and 0.0005 g/l $MnSO_4$ in a 2 liter baffled shaker flash at pH 7 and 37° C. The 350 ml culture was used to inoculate 4.2 liters of fermentation media containing 1% glucose, 13.2 g/l $Na_2HPO_4-7H_2O$, 3.0 g/l $KH_2PO_4$, 0.05 g/l NaCl, 1.0 g/l $NH_4Cl$, 10.0 g/l Casamino Acids (Difco), 0.03 g/l $MgSO_4$, 0.004 g/l $CaCl_2-2H_2O$, 0.025 g/l Thiamine-HCl, 0.0054 g/l $FeCl_3$, 0.0004 g/l $ZnSO_4$, 0.0007 g/l $CoCl_2$, 0.0007 g/l $Na_2MoO_4$, 0.0008 g/l $CuSO_4$, 0.0002 g/l $H_2BO_3$, and 0.0005 g/l $MnSO_4$.

Bacterial cells were harvested employing a membrane cell-concentrator and a high speed centrifuge immediately after completion of the fermentation. The fermented cell broth was concentrated from 5 liter to approximately 800 ml employing a 0.45 micron (μm) membrane filter (2 square feet). The cell concentrate was then centrifuged at 7,000×g for 10 minutes in a refrigerated centrifuge. The bacterial cell pellets are recovered after discarding the supernatant.

Plasmid DNA was extracted from bacterial cell pellets. The cells were thoroughly resuspended in 3 times the cell pellet mass (M) (in milliliters) of a solution containing 50 mm glucose (filter sterilized), 10 mM NaEDTA (pH 7.5-8.0), and 25 mm Tris-HCl (pH 8.0). The cells were lysed with vigorous swirling after the addition of 6×M (in milliliters) in a solution containing 0.2M NaOH, and 1% (w/v) sodium dodecylsulfate (SDS) . When the solution cleared, 4.5×m (in milliliters) of a solution containing 55.5 ml of glacial acetic acid and 147.5 grams of potassium acetate in a final volume of 500 ml was mixed thoroughly resulting in the production of a flocculent precipitate. The supernatant was separated from the flocculent precipitate and this supernatant centrifuged for 15 minutes at 7000×g to remove residual precipitate.

Nucleic acid was precipitated from the supernatant with one volume of ethanol followed by centrifugation for 10 minutes at 7000×g. and the nucleic acid pellets were resuspended in a total of 0.54×M (in milliliters). The nucleic acid was then extracted with ½ volume of neutralized phenol and ½ volume of chloroform and precipitated with two volumes of ethanol. The nucleic acid was resuspended in 0.3×M (in milliliters) of a solution of 50 Mm Tris HCl (pH 7.0) and 100 mM sodium acetate. 0.77×M (in microliters) of 10 mg/ml RNase (heat treated) was then added and allowed to digest for 30 minutes at room temperature or overnight at 4° C. 0.615×m (in microliters) of a solution of Proteinase K (20 mg/ml) was then added and incubated at 55° C. for three hours. DNA was extracted with ½ volume of neutralized phenol and ½ volume of chloroform and precipitated with two volumes of ethanol.

DNA was resuspended in 0.415×M (in milliliters) of water, and 0.05×M milliliters of 5M NaCl and 0.155×M milliliters of 50% (w/v) polyethyleneglycol (PEG) (molecular weight 6000-8000) were added, incubated on ice water for one hour and precipitated by centrifugation for 15 minutes at 7,000×g. The DNA was resuspended in 0.04×M milliliters of water and 1/10 volume of 3M sodium acetate and extracted with ½ volume of neutralized phenol and ½ volume of chloroform and precipitated with two volumes of ethanol. The purified DNA was resuspended in 0.0476×m milliliters of deionized $H_2O$. The DNA concentration was determined by fluorometry.

Finally, the purified DNA was disrupted into small fragments of approximately 300 base pairs by sonication using a Branson Sonifier 450 (Danbury, Conn.). This size of fragments has been empirically determined to be the optimum for DNA probes used for in situ hybridization. Four milligrams of the purified plasmid DNA prepared above was resuspended in 2 mls of water and immersed in a dry ice/ethanol bath to prevent boiling during sonication. The microtip of the sonication device was immersed in this solution until the tip was 2-5 mm from the bottom of the tube. Sonication was carried out at an output power of 25-30 watts, discontinuously, with an 80% duty cyle (on 80% of time, off 20% of time), for a period of 5 minutes. Following sonication, the DNA was precipitated by the addition of 0.2 ml of 3M sodium acetate (pH 5.5) and 4 ml of ethanol. The precipitate was recovered by centrifugation for 5 minutes at 8,000×g and vacuum dried.

EXAMPLE 2

Bisulfite Catalyzed Transamination of DNA

DNA was transaminated by the addition of ethylenediamine to the C4 carbon atom of the base cytosine. This reaction is catalyzed by sodium bisulfite. Approximately 3 to 6% of the available deoxycytidine nucleotide sites are aminated for labeling with dinitrophenylated amino acids, particularly 6-N-(2,4-dinitrophenylamino)caproic acid -O-(N-hydroxysuccinimide)-3-sulfonate and 6-N-(2,4-dinitrophenylamino) glycyl-glycylglycyl-O-(N-hydroxysuccinimide)-3-sulfonate.

To prepare the bisulfite buffer, 1.7 ml of fuming HCl was slowly added to 1 ml deionized $H_2O$ on ice. 1 ml fresh ethylenediamine (Sigma cat. #E-4379) was then slowly added on ice. After dissolution of the ethylenediamine, the solution was warmed to room temperature and 0.475 g sodium metabisulfite (Aldrich Cat. #25,555-6) was added. Fuming HCl was then slowly added to the bisulfite mixture until the pH reached 7.0. Deionized water was added to a funal volume of 5.0 ml.

To transaminate DNA, 1 milligram of sonicated DNA was resuspended in 0.3 ml $H_2O$. The DNA was denatured by boiling at 100° C. for 5 minutes then quickly chilled in an ice water bath. The transamination reaction was initiated by the addition of 0.3 ml of this DNA solution to 2.7 ml of bisulfite buffer, and the reaction was incubated at 37° C. for 2 days. The DNA solution was desalted by routine dialysis against 5-10 mM sodium borate (pH 8.0). After dialysis, 0.3 ml of 3M sodium acetate (pH 5.5) was added to the dialysate. The aminated DNA was precipitated with 2.5 volumes of ethanol and recovered after centrifugation at 8,000×g for 10 minutes. The pellets were vacuum dried and rehydrated at a concentration of 3 mg/ml DNA. This solution was stored at −80° C. until use.

EXAMPLE 3

Preparation of Nitrophenyl Derivatives of Amino Acids

A solution of 20 mM ε-amino-n-caproic acid was prepared by adding 2.62 g of this compound to 20 ml water containing 40 mmol sodium bicarbonate. This solution was mixed with 20 ml of a 20 mM solution of Sanger's reagent (2,4 dinitro-fluorobenzene) and allowed to stand at room temperature for 1 hour. The mixture was then gently heated, which caused the solution to turn yellow and a small amount of the dissolved sodium bicarbonate to precipitate. This precipitate was re-dissolved by the addition of a sufficient quantity of concentrated HCl and then left at 4° C. to induce crystallization. The crystals were collected in vacuo and washed with water to yield 4.2 g of yellow crystalline ε-dinitrophenylamino-n-caproic acid (DNP-NCA).

DNP-NCA was activated by esterification to 3-sulfo-N-hydroxysuccinimide as follows. 0.594 g of DNP-NCA, 0.468 g dicyclohexylcarbodiimide and 0.434 g of 3-sulfo-N-hydroxysuccinimide were vigorously stirred in 7 ml dimethylformamide at room temperature overnight. This reaction was determined to have gone >90% to completion by thin layer chromatography. The mixture was cooled to 0° C. and stirred for an additional hour. The mixture was then filtered and the yellow solution evaporated to a thick yellow oil which did not crystallize. This oil was stirred with 50 ml ethanol to yield 0.996 g of a fine yellow powder which was collected by filtration and washed with ethanol. This compound is 6-N-(2,4-dinitrophenylamino)caproic acid-O-(N-hydroxysuccinimide)-3-sulfonate (sodium salt) and will be referred to for the purposes of this invention as S-NHS-DNP.

EXAMPLE 4

Preparation of Nitrophenyl Derivatives of Naturally Occurring and Synthetic Peptides The dinitrophenyl derivative of the peptide Gly-GlyGly was prepared by mixing 3.78 g of the peptide (20 mmol) with 3.72 g of Sanger's reagent in a total volume of 1 ml/mmol of peptide of a solution of 40 mmol sodium bicarbonate at room temperature for 3 hours. The solution was warmed initially to 40°-50° C. to initiate the reaction. Sufficient concentrated HCl was added to re-dissolve the slight sodium bicarbonate precipitate which formed, and then the mixture was incubated at 4° C. to induce crystal formation. The resulting crystals were filtered in vacuo, washed with 1M HCl and air dried to yield 6.99 g of dinitrophenyl amino glycylglycylglycine (DNP-GGG).

DNP-GGG was activated by esterification to 3-sulfo-N-hydroxysuccinimide as follows. 1.42 g of DNP-GGG, 0.941 g dicyclohexylcarbodiimide and 0.868 g of 3-sulfo-N-hydroxysuccinimide were vigorously stirred in 10 ml dimethylformamide at room temperature overnight. The mixture was cooled to 0° C. and stirred for an additional hour. The mixture was then filtered and the solution evaporated to remove DMF. The thick yellow non-crystalline oil was stirred with 50 ml ethanol to yield 2.26 g of a fine yellow powder, which was collected by filtration, washed with ethanol and dried in vacuo over Drierite. This compound, is (2,4-dinitrophenyl)aminoglycylglyclyglycine-O-(N-hydroxysuccinimide)-3-sulfonate (sodium salt) and will be referred to for the purposes of this invention as S-NHS-GGG-DNP.

EXAMPLE 5

DNA Labeling: DNP-Deriviatived ε-amino-n-caproic Acid

Chromosome-specific DNA probes to human chromosome 1 of average length of about 300 bp obtained by the procedure of Example 1 were derivatized by the bisulfite catalyzed transamination with ethylenediamine as described in Example 2. Approximately 5% of the bases were aminated. A solution of aminated DNA (100 μg total DNA) in a plastic 1.5 ml centrifuge tube was evaporated under reduced pressure. To this solution was added 0.5 ml of 0.2M 3-[N-morpholino] propane sulfonic acid (MOPS) buffer and then 100 microliters of S-NHS-DNP (30 mg/ml N,N-dimethylformamide) was added to the residue and the mixture was incubated overnight at 25° C. Labeled DNA was precipitated by the addition of 60 μl of 3M sodium acetate (pH 5.5) followed by 1.5 ml of ice cold ethanol and the mixture was incubated for at least 2 hours at −20° C. The solution was subjected to centrifugation for 10 minutes at 10,000×g. The DNA pellet was washed twice with 0.6 ml of ice cold ethanol and then dissolved in 100 μl of sterile water. Two Sephadex G-50 Select D chromatography columns (5 Prime→3 Prime, Inc.) with a bed volume of 0.8 ml were prepared. 50 μl of the dissolved pellet was applied to each column and centrifuged for 4 minutes at 10,000×g. 10 μl of the purified DNA was diluted with 490 μl of 20 mm NaOH and the optical density was determined at 260 nm to assess DNA concentration. The purified DNA was diluted with water to provide a working concentration of DNA of 100 micrograms per ml.

In situ Hybridization Procedure

The DNP-labeled DNA probe was tested by in situ hybridization. The target DNA consisted of cultured normal white blood cells that were arrested in metaphase. The cells were dropped onto a glass microscope slide from a distance of about three feet to break open the nuclei. Before hybridization, the slide was placed in a denaturing solution of 70% formamide/0.3M NaCl/30 mM sodium citrate (pH 7) at 70° C. The slide as then dehydrated by passage through solutions of 70%, 85% and 100% ethanol (2 min each).

The hybridization mixture that was placed on each slide consisted of 50% formamide/0.3M NaCl/30 Mm sodium citrate (pH 7). Human placental DNA (2.25 micrograms/10 microliters) was used as blocking DNA. The DNP-labeled DNA was added at a concentration of 10 ng/μl. Ten microliters of the complete hybridization mixture was denatured by heating at 70° C. for 10 minutes. The probe and blocking DNA was prehybridized for 60 minutes at 37° C. The mixture as then applied to the slide, covered with a coverslip and sealed with rubber cement. Hybridization proceeded overnight at 37° C. in a humidified chamber.

The next day, the excess probe was removed by washing the slide three times for 15 minutes at 45° C. in 50% formamide/0.3M NaCl/30 mM sodium citrate (pH 7), then in 0.3M NaCl/30 Mm sodium citrate (pH 7) and in 0.1M sodium phosphate (pH 7)/0.1% NP40 detergent (octylphenoxypolyethoxyethanol, which is a non-ionic surfactant sold by Calbiochem, La Jolla, Calif.) (PN buffer) each for 15 minutes at 45° C. The slide was washed 2 times in PN buffer at 25° C., 2 minutes each wash. The slide was incubated 20 minutes at 25° C. in rabbit anti-DNP (Sigma) diluted 1:250 in PNM buffer. PMN buffer is 0.1M sodium phosphate (pH 7)/0.1% NP40 detergent/0/5% nonfat dry milk. The slide was washed in PN buffer, 3 times for 2 minutes each at 25° C. The slide was then incubated for 20 minutes alkaline phosphatase-antirabbit immunoglobulin G (Sigma) diluted 1:250 in PNM buffer. The slide was washed in PN buffer 3 times for 2 minutes each at 25° C. The slide was then incubated in 17 ml of BCIP/NBT [a solution containing 4 μl/ml of nitro blue tetrazolium (NBT) and 3 mg/ml of 5-bromo-4-chloro-3-indolyl-phosphate (BCIP, as provided by Chemprobe)] for 30 minutes at 37° C. The slide was rinsed in distilled water, air dried, and viewed with a microscope.

In situ Hybridization Results

The alkaline phosphatase label catalyses the conversion of the BCIP/NBT substrate into a dark blue dye which appears black when viewed with the microscope. Nontarget chromosomes either appear colorless or can be counterstained blue with a Giemsa stain preparation.

Following substantially the above procedures, results for Chromosomes 2, 4, 6 and 12 were also obtained.

| Chromosome Number | Visual Description | |
|---|---|---|
| | Specificity | Intensity |
| 1 | +++ | +++ |
| 2 | +++ | +++ |
| 4 | +++ | +++ |
| 6 | +++ | +++ |
| 12 | +++ | ++ |

Code:
Specificity: (−) none apparent, (+) slightly heavier staining in target chromosomes, (++) reasonable specificity, (+++) good specificity.
Intensity: (−) not visible, (+) visible under phase only, (++) dark staining, visible under transmission, (+++) very dark staining, refractile under phase.

We claim as our invention:

1. A reagent for in situ detection of nucleic acid sequences comprising one or more DNA sequences complementary to the nucleic acid sequences to be detected wherein the DNA sequences include at least one transamination site and multiple labels comprising phenyl substituted with one to three nitro groups each multiple label being covalently linked to said transamination site by an amino acid linking group.

2. The reagent according to claim 1 wherein said linking group is comprised of lower alkyl amino acids and polymers and copolymers thereof.

3. The reagent according to claim 1 wherein the phenyl label is 4-nitrophenyl.

4. The reagent according to claim 1 wherein the phenyl label is 2,4-dinitrophenyl.

5. The reagent according to claim 1 wherein the phenyl label is 2,4,6-trinitrophenyl.

6. The reagent according to claim 1 wherein the DNA sequences prior to labeling are obtained from a recombinant phage library of the chromosome or chromosome region to be detected.

7. The reagent according to claim 6 wherein the DNA sequences have an average length of about 300 bp.

8. The reagent according to claim 1 wherein the labels are covalently linked to the DNA sequences at aminated cytosine sites.

9. The reagent according to claim 8 wherein about 5-50% of cytosine sites in the DNA sequences are aminated by bisulfite catalyzed transamination with a diaminoalkane having 2 to 10 carbon atoms.

10. The reagent according to claim 1 wherein about 3-6% of bases in the DNA sequences are labeled.

11. The reagent according to claim 1 wherein the number of labels is sufficient to be detected by immunological techniques while retaining the specific binding properties of the DNA with respect to the complementary target sequence or sequences to be detected.

12. The reagent according to claim 1 wherein the label is formed by reacting the DNA with 6-N-(2,4-dinitrophenyl) caproic acid-O-(N-hydroxysuccinimidyl-3-sulfonate) ester or N-(2,4-dinitrophenyl) glycylglycylglycine-O-(N-hydroxysuccinimidyl-3-sulfonate) ester.

13. A method for making a reagent for in situ detection of a chromosome or region of a chromosome comprising:
   (a) disrupting plasmid DNA containing DNA complementary to the chromosome or region of chromosome to be detected into fragments,
   (b) transaminating the DNA fragments, and
   (c) covalently linking a label comprising phenyl substituted with one to three nitro groups, said labels covalently linked thereto by means of an amino acid linking group.

14. The method of claim 13 wherein the plasmid DNA is disrupted by sonication into fragments of average length of about 300 bp.

15. The method of claim 13 wherein the DNA fragments are transaminated by bisulfite catalyzed transamination with ethylenediamine.

16. The method of claim 13 wherein the label is formed by reaction of DNA with 6-N-(2,4-dinitrophenyl) caproic acid-O-(N-hydroxysuccinimidyl-3-sulfonate) ester or N-(2,4-dinitrophenyl) glycylglycylglycine-O-(N-hydroxysuccinimidyl-3-sulfonate) ester.

17. A reagent for in situ detection of a chromosome or region of a chromosome comprising unhybridized DNA sequences having essentially complementary base sequences with respect to different portions of the chromosome or chromosome region to be detected and having a plurality of cytosine bases that are transaminated, a number of the transaminated cytosine bases having a label comprising phenyl substituted with one to three nitro groups, said labels covalently linked thereto by means of an amino acid linking group, the number of labeled cytosine bases being sufficient for detection by immunological techniques while essentially retaining the specific binding properties of the reagent with respect to the chromosome or chromosome region to be detected.

18. The reagent according to claim 17 wherein the DNA sequences prior to labeling are obtained from a recombinant phage library of the chromosome or chromosome region to be detected.

19. The reagent according to claim 18 wherein the DNA sequences have an average length of about 300 bp.

20. The reagent according to claim 17 wherein about 5-25% of cytosine sites in the DNA sequences are aminated by bisulfite catalyzed transamination with ethylenediamine.

21. The reagent according to claim 20 wherein about 1-5% of the bases in the DNA sequences are labeled.

22. The reagent according to claim 21 wherein the label is formed by reacting the DNA with 6-N-(2,4-dinitrophenyl) caproic acid-O-(N-hydroxysuccinimidyl-3-sulfonate) ester or N-(2,4-dinitrophenyl) glycylglycyl-lycine-O-(N-hydroxysuccinimidyl-3-sulfonate) ester.

23. A method for preparing a reagent for in situ detection of a chromosome or region of a chromosome comprising:
   (a) transaminating a number of cytosine bases contained in unhybridized DNA sequences having essentially complementary base sequences with respect to the chromosome or chromosome region to be detected; and
   (b) covalently bonding labels comprising phenyl substituted with one to three nitro groups, said labels covalently linked thereto by means of an amino acid linking group, to at least a portion of the transaminated bases, the portion of cytosine bases having labels covalently bonded thereto being sufficient to be detected by immunological techniques while essentially retaining the specific binding properties of the reagent with respect to the chromosome or chromosome region to be detected.

24. The method of claim 23 wherein the cytosine bases are transaminated by bisulfite catalyzed transamination with ethylenediamine.

25. A method for labeling DNA comprising transaminating one or more cytosines in the DNA with an alkylenediamine containing 2 to 9 carbon atoms and reacting the transaminated DNA with 6-N-(2,4-dinitrophenyl) caproic acid-O-(N-hydroxysuccinimidyl-3-sulfonate) ester or N-(2,4-dinitrophenyl) glycylglycylglycine-O-(N-hydroxysuccinimidyl-3-sulfonate) ester.

26. A reagent comprising DNA having one or more dinitrophenyl groups covalently bound to the bases therein by means of an activated derivative of a lower alkyl amino acid wherein the dinitrophenyl is detectable by immunological techniques and the DNA retains its essential binding properties.

27. A reagent according to claim 26 comprising DNA in which one or more cytosine bases is transaminated with an alkylene diamine containing 2 to 9 carbon atoms and the transaminated DNA is reacted with 6-N-(2,4-dinitrophenyl) caproic acid-O-(N-hydroxysuccinimidyl-3-sulfonate) ester or N-(2,4-dinitrophenyl) glycylglycylglycine-O-(N-hydroxysuccinimidyl-3-sulfonate) ester.

28. A reagent according to claim 27 wherein the DNA is transaminated by bisulfite catalyzed transamination with ethylenediamine.

29. A method for preparing a reagent for labeling DNA comprising the following steps:

(a) reacting an amino acid linking group with labels comprising phenyl substituted with one to three nitro groups so as to form a covalent linkage;
(b) activating the resulting label-linker compound by esterification to 3-sulfo-N-hydroxysuccinimide; and
(c) covalently bonding the activiated label-linker compound to transaminated DNA.

30. The method of claim 29 wherein the amino acid linking group is comprised of lower alkyl amino acids and polymers and copolymers thereof.

* * * * *